United States Patent [19]

Rice

[11] Patent Number: 4,556,712
[45] Date of Patent: Dec. 3, 1985

[54] PREPARATION AND RACEMIZATION OF CHIRAL 1-BENZYL-1,2,3,4-TETRAHYDROISOQUINOLINES

[75] Inventor: Kenner C. Rice, Rockville, Md.

[73] Assignee: The United States of America as represented by the Secretary of the Department of Health and Human Services, Washington, D.C.

[21] Appl. No.: 476,830

[22] Filed: Mar. 18, 1983

Related U.S. Application Data

[63] Continuation-in-part of Ser. No. 265,469, May 20, 1981, which is a continuation-in-part of Ser. No. 165,690, Jul. 3, 1980, abandoned.

[51] Int. Cl.⁴ ............................................ C07D 217/20
[52] U.S. Cl. .................................... 546/149; 546/44; 546/18; 546/74; 564/139
[58] Field of Search ........................................ 546/149

[56] References Cited

U.S. PATENT DOCUMENTS

| | | | |
|---|---|---|---|
| 2,819,272 | 1/1958 | Den Hollander | 546/149 |
| 2,915,479 | 12/1959 | Den Hollander | 546/149 |
| 3,810,899 | 5/1974 | Mohacsi | 546/149 |
| 3,855,227 | 12/1974 | Den Hollander et al. | 424/258 |
| 3,894,027 | 7/1975 | Sohar et al. | 424/258 |
| 3,985,881 | 10/1976 | Mehrhof | 424/258 |
| 4,024,082 | 5/1977 | Partyka et al. | 424/250 |
| 4,115,389 | 9/1978 | Monkavic . | |
| 4,194,044 | 3/1980 | Mohacsi | 546/146 |
| 4,247,697 | 1/1981 | Mohacsi | 546/74 |
| 4,410,700 | 10/1983 | Rice | 546/149 |

OTHER PUBLICATIONS

Beyerman et al., Synthesis of Racemic and Optically Active Codiene and Morphine. . ." *J. Royal Neth. Chem. Soc.* 97, pp. 127–130, (1978).
Brossi et al., "Synthesis . . . Isoquinoline Series . . . ," *Helv. Chim. Acta* 44: 1558–1565, (1961).

*Primary Examiner*—Donald G. Daus
*Assistant Examiner*—G. Hendricks
*Attorney, Agent, or Firm*—John S. Roberts, Jr.

[57] ABSTRACT

In a short total synthesis of morphinan compounds, derivatives of 1-benzyl-1,2,3,4-tetrahydroisoquinoline are produced. Certain of these compounds, although highly aromatic and functionalized, can be optically resolved. The optically active enantiomers can serve as important intermediates for both natural and unnatural opioids.

10 Claims, No Drawings

PREPARATION AND RACEMIZATION OF CHIRAL 1-BENZYL-1,2,3,4-TETRAHYDROISOQUINOLINES

CROSS REFERENCE

This application is a continuation in part of pending U.S. Ser. No. 265,469 filed May 20, 1981, which is a continuation in part of U.S. Ser. No. 165,690 filed July 3, 1980, now abandoned.

PRIOR ART

U.S. Pat. No. 2,819,272 DenHollander (Hoffmann-LaRoche) and U.S. Pat. No. 2,915,479 DenHollander (Hoffman-LaRoche) pertain to octahydro derivatives and they differ by the fact that they have only one aromatic ring and the present invention has two. Both aromatic rings are more highly functionalized in the series of the present invention. There is no indication of carryover of teaching from the known patents to the present application.

U.S. Pat. No. 3,810,899 Mohacsi et al (Hoffmann-LaRoche), confer column 7.

U.S. Pat. No. 3,914,232 Mohacsi et al (Hoffmann-LaRoche) deals with the racemization of octahydroisoquinolines. This differs from the present invention in that it is a much less functionalized system and has only one aromatic ring, whereas the present invention has two.

U.S. Pat. No. 3,914,233 Mohacsi et al (Hoffmann-LaRoche).

British No. 1,330 581 Merck & Co. is of general interest.

Yamaguchi et al, Yakugaku Zasshi, 82:552 (1962), abstracted in Optical Resolution Procedures for Chemical Compounds, Volume 1, Amines and Related Compounds, by Paul Newman, Optical Resolution Information Center, Riverdale, N.Y., page 398—the solvent and conditions for this isoquinoline differ substantially from the present invention.

Kametani et al, J. Chem. Soc., 1968, pp. 1619–1620, deals with racemization of a tertiary amine rather than the secondary amine of the present invention.

Kametani et al, Heterocycles, Vol. 5, 1976, pp. 649–668.

Beyerman et al, Recl. Trav. Chim. Pays-Bas, 97:127 (1978) describes a process directed to a rather esoteric method which additionally uses time encompassing protecting intermediates.

The following references discuss the importance of (+)-opioids for antitussive agents and neuropharmacological research tools:

Takagi et al, Yakugaku Zasshi, 80:1506 (1960).

T. T. Chan and L. S. Harris, J. Pharm. Exp. Ther., 215:668 (1980).

I. Iijima, et al, J. Med. Chem., 21:398 (1978) and references cited therein.

BACKGROUND OF THE INVENTION

The present application relates to production of chiral intermediates for total synthesis of (−)- and (+)-opioids by the method disclosed in U.S. patent application Ser. No. 165,690 filed July 3, 1980. Since all medically important opium derivatives, including thebaine, can be manufactured from intermediates prepared in the above-mentioned disclosure, the simple and effective methods described below for synthesis of chiral precursors are of fundamental importance. In addition to affording intermediates for production of (−)-opioids (natural), the present disclosure also permits synthesis of intermediates useful for preparing (+)-opioids which are of importance as antitussive agents and neuropharmacological research tools.

The synthesis outlined for the total short synthesis of dihydrothebainone, dihydrocodeinone, and nordihydrododeinone is shown schematically in the following outline.

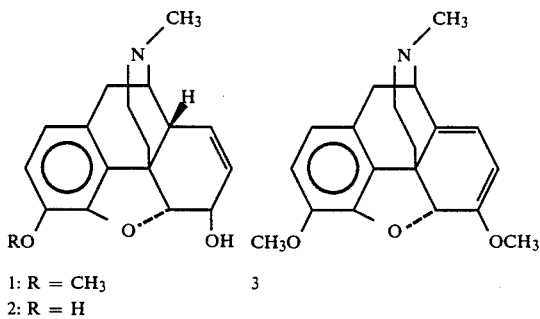

1: R = CH₃
2: R = H
3

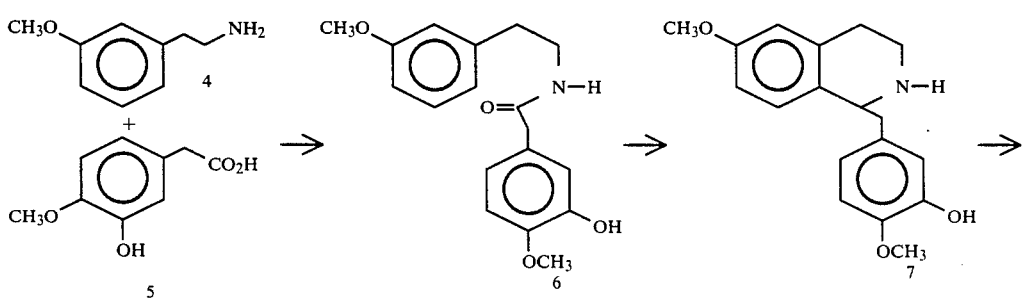

5
6
7

-continued

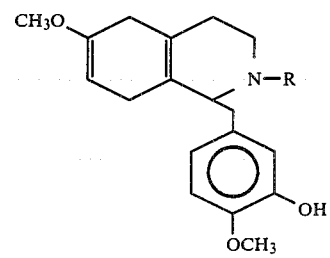

8: R = H
9: R = CH₃
10: R = CHO

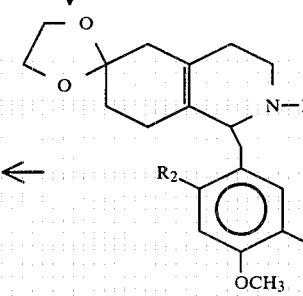

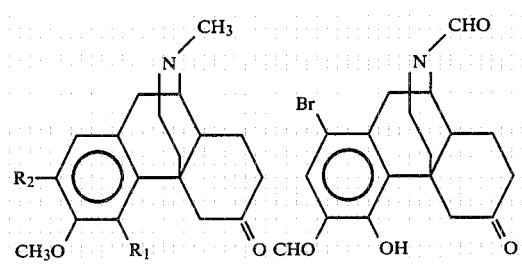

19: R₁ = OH, R₂ = H        17
20: R₁ = H, R₂ = OH

13: R = CHO    11: R₁ = CHO, R₂ = H
14: R = H      12: R₁ = CHO, R₂ = Br

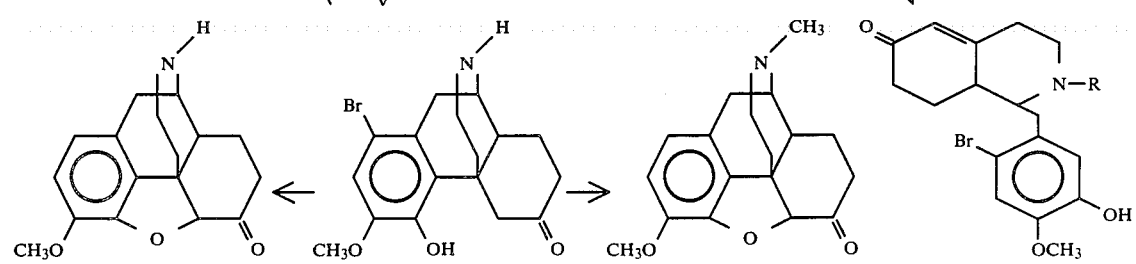

21     18     22     15: R = H
                     16: R = CHO

As a general summary of the above chart, the following general description is made commencing with codeine (1).

Racemic dihydrothebainone (19), nordihydrocodeinone (21) and dihydrocodeinone (22) were synthesized in high overall yield from 3-methoxyphenethylamine (4), via the key intermediate (±)-1-bromonordihydrothebainone (18); the route utilized unprotected phenolic intermediates, involved directed Grewe-type cyclization and for 21 and 22, exploited novel oxide bridge closure in the N-nor series.

Heating a mixture of amine (4) and pure acid (5) afforded amide (6). Cyclization of 6 generated an aqueous solution of the 1,2-dihydro derivative of 7, not shown on the chart. This derivative is the starting point for the novel asymmetric synthesis of this invention. (The possibility for resolution of racemic tetrahydroisoquinoline 7 is suggested in the parent application.)

Birch reduction with lithium and ammonia afforded 8. Refluxing 8 with PhOCHO or chloral gave 10. A solution of 10 and ethylene glycol generated a solution of ketal 11 and subsequently bromoketal 12 was produced. Grewe-type cyclization produced 17. Refluxing 17 in MeOH-aqueous HCl yielded 18. 19 is available from 17 by hydrogenation in the presence of formaldehyde. Synthesis routes from 18 yield 19, 21, and 22. Specific details are found in the parent application, incorporated by reference.

Conversion of (−)-19 to (−)-thebaine (3) and (−)-codeine (1) and facile O-demethylation of the latter to (−)-morphine (2) provide a practical total synthesis of these natural alkaloids.

SUMMARY OF THE INVENTION

The present invention provides for a facile optical resolution of phenolic 1-benzyltetrahydroisoquinoline 1' and ethers 2' and 3' (prime numbers refer to the following chart of compounds). This resolution thus makes available two optical forms and thereby the synthesis route previously discussed is utilized for the production of both natural (−)- and unnatural (+)-opioids.

The concept of formation and chromatographic separation of diasterisomers is well known. However, the compounds of interest herein are, unlike the prior art, highly aromatic and highly functionalized.

Optical resolution has also been empirical and highly individualized. Among the most difficult enantiomers to resolve are the phenolic secondary amines in the 1-benzyl-1,2,3,4-tetrahydroisoquinoline series. Even ten years ago resolution of these compounds depended on conversion to benzyl ethers and resolution therefrom. The prior art [Yamaguchi, H., et al., Yakugaku Zasshi, 82, 555 (1962)] for a phenolic secondary amine shows an acid and solvent quite different from the present invention.

It is well recognized that salt formation and solubility parameters are very critical and much experimentation is necessary to find the proper combination for each individual resolution.

The present invention also encompasses racemization of either enantiomer of 1' and derivatives so that, if desired, one enantiomer can be produced to the exclusion of the other by recycle of the racemate. Racemization can be accomplished by catalytic hydrogenation of the chiral 1-benzyl-1,2,3,4-tetrahydroisoquinoline with metal catalysts such as palladium, platinum, nickel and cobalt. Platinum and palladium catalysts in solvents such as alkanoic acids, ethers, and hydrocarbons are preferred. Simple filtration of the catalysts and workup by evaporation of the solvent affords the racemate in high chemical yield. Also, oxidation of 1-benzyltetrahydroisoquinolines, lower alkoxy and acyloxy derivatives (see chart) with reagents such as N-chlorosuccinamide, sodium hypochlorite, sodium hypobromite, and lower alkyl hypochlorites and hypobromites, and treatment with base to give dehydro intermediate of type 4'-6', followed by reduction with sodium cyanoborohydride or sodium borohydride can be used to effect racemization of 1'-3'. Synthesis of 4' and sodium cyanoborohydride reduction of 4' to 1' were described in application Ser. No. 165,690 Rice, ante.

A further aspect of the invention consists of asymmetric reduction of intermediates 4'-6' to give 1'-3'. For this reduction process either asymmetric catalytic hydrogenation or chemical reduction may be used.

For catalytic reduction, hydrogenation of 4'-6' using rhodium complexes with chiral ligands such as DIPAMP, CHIROPHOS or NORPHOS (available from Reaction Design, Hillside, N.J.) are used in alkanols, alkanol ethers, water or mixtures thereof. U.S. Pat. No. 3,849,480 describes asymmetric hydrogenation, catalysts and process steps. These catalysts have been used quite successfully in asymmetric hydrogenation of azalactones to eventually afford optically active amino acids. Intermediates of the type 7'-9' which are easily available from 4'-6' by standard methods are ideal for asymmetric hydrogenation to the N-acetyl derivatives of 1'-3'. The 1'-3' can then be obtained by standard acid or alkaline hydrolysis of the acetyl group(s) or the chiral N-acyl derivatives can be utilized directly for further reaction.

For chemical reduction of 4'-6' to 1'-3', chiral boranes such as diisopinocampheylborane derived from the readily available (+) and (−)-pinene and other chiral boranes may be employed in ether-type solvents such as tetrahydrofuran, glyme (dimethyl ether of ethylene glycol) and diglyme. Also, chemical reduction with sodium borohydride and sodium cyanoborohydride in reaction media such as aqueous or aqueous alcoholic chiral tartrate-phosphate buffer systems may be employed. By utilization of either (+)- or (−)-tartaric, malic or other optical pairs of organic acid either enantiomer of 1'-3' may be obtained.

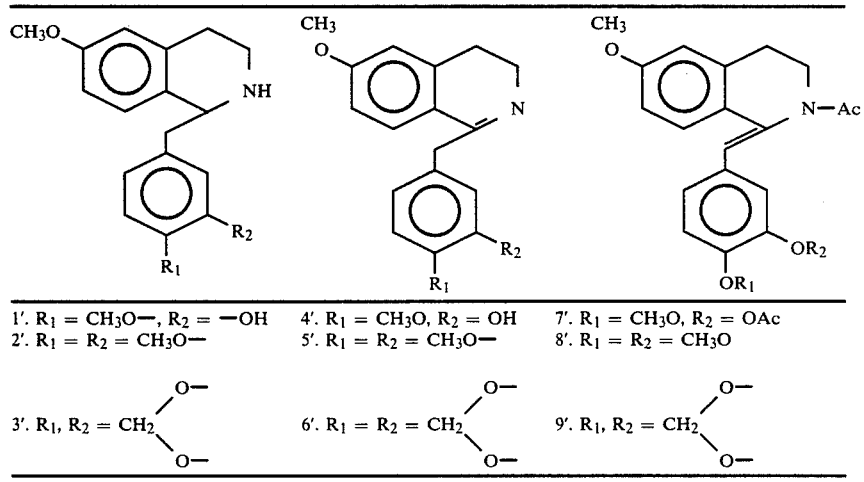

1'. $R_1 = CH_3O—$, $R_2 = —OH$
2'. $R_1 = R_2 = CH_3O—$
3'. $R_1, R_2 = CH_2\begin{smallmatrix}O—\\O—\end{smallmatrix}$ 4'. $R_1 = CH_3O$, $R_2 = OH$
5'. $R_1 = R_2 = CH_3O—$
6'. $R_1 = R_2 = CH_2\begin{smallmatrix}O—\\O—\end{smallmatrix}$ 7'. $R_1 = CH_3O$, $R_2 = OAc$
8'. $R_1 = R_2 = CH_3O$
9'. $R_1, R_2 = CH_2\begin{smallmatrix}O—\\O—\end{smallmatrix}$

DETAILS OF THE INVENTION

Suitable optical acids include (+)- and (−)-malic, tartaric and tartranilic acid.

For the malic and tartaric acids, alkanols of 1-6 carbon atoms are suitable solvents and methanol is the preferred solvent. Water may be added. Dimethyl formamide (DMF) is used to improve the yield.

For the tartranilic acid, acetonitrile and methanol are used as solvent and DMF acts to improve the yield.

For the tartaric acid, the procedure is as follows. To the racemate, (+)-tartaric acid in methanol at 55° C. is added. The mole ratio of base to acid is approximately 1:1. The (−)-1′ base forms a salt that precipitates. The precipitate is heated to solution in DMF in which it is quite soluble and then diluted with methanol. The ratio of DMF to methanol is approximately 1:9. This method, based on a supersaturated solution, produces an almost quantitative yield. A second identical recrystallization is preferable to get a pure (−)-1′.(+)-tartaric salt, m.p. 134°–136° C.

The base (−)-1′ is regenerated with aqueous 50% (v/v) methanol and concentrated aqueous ammonia. The solid base is washed with water, isopropanol and has the following properties: m.p. 218°–219.5° C. $[\alpha]_D^{23} -37.7°$ (c 0.26 DMF).

The pooled filtrates are used to generate the (+)-1′ base. The filtrates are evaporated, dissolved in 50% methanol at 55° C. with aqueous ammonia to generated mixed bases. This is the same procedure for regenerating all bases and the washings use water, isopropanol, and ether.

Using (−)-tartaric acid with the base (mole ratio of about 1:1 acid to base) in methanol gives a rapidly deposited crystalline material. Cooling and washing gives a (+)-1′.(−)-tartaric acid of approximately 99% optical purity. Recrystallization from a supersaturated solution of DMF with methanol added (1:9 volumes) gives a very good yield of the salt. The salt is converted to base following the above procedures. The optically pure base, (+)-1′, has a m.p. 218.5°–220° C.; $[\alpha]_D^{23} +38.1°$ (c 0.27, DMF).

Chemical and optical purity is determined on HPLC as indicated in the examples.

The procedure with malic acid is similar to the above and similar results are obtained.

With nitrotartranilic acid, the (+)-2′-nitrotartranilic acid is used to precipitate a salt of (+)-1′.(+)-tartranilate. The solvent used is methanol first, then evaporation and acetonitrile. The volume of methanol to acetonitrile is 2–3:1. The precipitate is washed with acetonitrile.

The precipitate is recrystallized from a first solution of 1:1 DMF-CH₃CN (v/v), diluted with acetonitrile to give a very good yield. A second similar recrystallization is desirable. The salt (+)-1′.(+)-2′-nitrotartranilic has a m.p. of 195°–196.5° C. The regenerated base, (+)-1′, has a m.p. of 217.5°–219° C. and $[\alpha]_D^{23} = +37.8°$ (c 0.25, DMF).

The filtrates and washing are treated as in resolution with tartaric acid to regenerate the bases. Treatment of the base with (−)-2′-nitrotartranilic acid in 1:1 DMF/acetonitrile and diluted with acetonitrile to give a good quantitative yield of (−)-1′.(−)-2′-nitrotartranilic acid salt with a m.p. of 193°–195° C. Regeneration of the base, (−)-1′, gave a m.p. of 218°–219.5° C. and $[\alpha]_D^{23} = -38.1°$.

In the specification and claims the term alkanol means a C₁–C₆ alcohol and also may include water as an additive or alone.

EXAMPLE 1

A suspension of the unwanted 1-(3-hydroxy-4-methoxybenzyl)-6-methoxy-1,2,3,4-tetrahydroisoquinoline (5.0 g, 0.0015 mol) and N-chlorosuccinimide (2.5 g, 0.0018 mol) in CH₂Cl₂ (35 ml) is stirred 30 min. At this point a reddish-brown solution is present, and there is no starting material left by TLC. Toluene (35 ml) is added, and the CH₂Cl₂ is removed in vacuo. Then NaH (0.38 g, 0.016 mol) is added and the resultant mixture stirred 45 min. Afterwards, no starting material is present by TLC. Consequently, the mixture is treated with MeOH (35 ml) and solid NaBH₄ (0.60 g, 0.016 mol). The resultant mixture is stirred 45 min. The precipitate is collected and washed successively with H₂O, MeOH and Et₂O. After air drying, the pale yellow solid is suspended in 50% MeOH and treated with concentrated HCl until it dissolves (pH 0–1 by paper). Neutralization with concentrated NH₄OH causes a white precipitate. This is collected and washed as before. After drying, the white solid weighs 2.70 g (54%) and has mp 202°–205° C. That the material is racemic is verified by HPLC analysis (vide supra).

EXAMPLE 2

A cooled suspension of the unwanted optically active 1-benzyl-1,2,3,4-tetrahydroisoquinoline (15 mmoles) in chloroform is treated with 0.16 mmoles of chlorox (sodium hypochlorite) and stirred 30 min. then heated until no starting material remained by TLC. The lower reddish chloroform phase is separated, evaporated. Toluene (35 ml) is added, and the CH₂Cl₂ is removed in vacuo. Then NaH (0.38 g, 0.016 mol) is added and the resultant mixture stirred 45 min. Afterwards, no starting material is present by TLC. Consequently, the mixture is treated with MeOH (35 ml) and solid NaBH₄ (0.60 g, 0.016 mol). The resultant mixture is stirred 45 min. The precipitate is collected and washed successively with H₂O, MeOH and Et₂O. After air drying, the pale yellow solid is suspended in 50% MeOH and treated with concentrated HCl until it dissolves (pH 0–1 by paper). Neutralization with concentrated NH₄OH causes a white precipitate. This is collected and washed as before. After drying, the white solid weighs 2.70 g (54%) and has mp 202°–205° C. That the material is racemic is verified by HPLC analysis (vide supra).

EXAMPLE 3

Example 2 is rerun using 0.16 moles of sodium or potassium hypobromite.

I claim:

1. A method for the optical resolution of lower alkoxy 1-benzyl-1,2,3,4-tetrahydroisoquinolines comprising the steps of
   (a) forming an insoluble (−)-isoquinoline base salt with an optically active acid selected from the group consisting of enantiomers of tartaric and malic with alkanol as a solvent and which is capable of regeneration to the (−)-isoquinoline base, and
   (b) utilizing the soluble salt to regenerate (+)-isoquinoline base which is reacted with an acid selected from the group consisting of enantiomers of tartaric and malic with alkanol as a solvent to form an insoluble salt which is capable of regeneration to the (+)-isoquinoline base.

2. The method of claim 1 in which the insoluble salts are recrystallized from supersaturated solutions of dimethyl formamide and alkanol is added to yield the insoluble salt.

3. A method for the optical resolution of lower alkoxy 1-benzyl-1,2,3,4-tetrahydroisoquinolines comprising the steps of
   (a) reacting the isoquinoline with (+)-optical acid of tartaric in methanol,
   (b) isolating the precipitate of (−)-isoquinolino-(+)-tartaric acid salt and reserving the filtrate,
   (c) heating the precipitate in DMF to form a solution, (d) adding alkanol to recrystallize the precipitate and and reserving the filtrate,
(e) regenerating the (−)-1-benzyl-1,2,3,4-isoquinoline base,
(f) collecting all filtrates, evaporating and solubilizing in methanol with ammonia to regenerate quinoline base,
(g) adding (−)-optical acid of tartaric acid to form a second precipitate of (+)-isoquinolino-(−)-tartrate,
(h) heating the second precipitate in DMF to form a solution and recrystallizing the precipitate by adding methanol,
(i) regenerating the (+)-1-benzyl-1,2,3,4-isoquinoline base.

4. A method for the optical resolution of lower alkoxy 1-benzyl-1,2,3,4-tetrahydroisoquinoline comprising the steps of:
(a) reacting the isoquinoline with (+)-optical acid of malic acid in alkanol,
(b) isolating the precipitate of (−)-isoquinolino-(+)-malic acid salt and reserving the filtrate,
(c) heating the precipitate in DMF to form a solution,
(d) adding alkanol to recrystallize the precipitate and reserving the filtrate,
(e) regenerating the (−)-1-benzyl-1,2,3,4-isoquinoline base,
(f) collecting all filtrates, evaporating and solubilizing in alkanol with ammonia to regenerate isoquinoline base,
(g) adding (−)-optical acid of malic acid to form a second precipitate of (+)-isoquinolino-(−)-malate,
(h) heating the second precipitate in DMF to form a solution and recrystallize the precipitate by adding methanol,
(i) regenerating the (+)-1-benzyl-1,2,3,4-tetrahydroisoquinoline.

5. A method of claim 3 wherein the volume ratio of DMF to methanol is approximately 1:9.

6. The method of claim 3 wherein steps (c) and (d) are repeated sequentially.

7. A method for the optical resolution of lower alkoxy 1-benzyl-1,2,3,4-tetrahydroisoquinolines comprising the steps of:
(a) forming an insoluble (+)-base salt with (+)-2'-nitrotartranilic acid from a solvent of alkanol and acetonitrile and
(b) regenerating the (+)-base and then regenerating the (−)-base from the soluble salt and forming an insoluble salt of (−)-base with (−)-2'-nitrotartranilic acid and regenerating the (−)-isoquinoline base therefrom.

8. The process of claim 7 wherein the salts are recrystallized using supersaturated solutions of dimethylformamide and acetonitrile.

9. A method for the optical resolution of lower alkoxy 1-benzyl-1,2,3,4-tetrahydroisoquinolines comprising the steps of:
(a) reacting the racemate of the isoquinoline with (+)-2'-nitrotartranilic acid to form a precipitate of (+)-isoquinolino-(+)-2'-nitrotartranilate in a solvent of alkanol and acetonitrile and reserving the filtrate,
(b) heating the precipitate to solution in 1:1 DMF-CH$_3$CN,
(c) recrystallizing the precipitate by adding acetonitrile and reserving the filtrate,
(d) regenerating the (+)-1-benzyl-1,2,3,4-tetrahydroisoquinoline,
(e) collecting all filtrate, evaporating and solubilizing in methanol and rendering alkaline to regenerate isoquinoline bases,
(f) adding (−)-2'-nitrotartranilic acid in 1:1 DMF/acetonitrile and adding additional acetonitrile to form a precipitate of (−)-isoquinoline-(−)-2'nitrotartranilate,
(g) recrystallizing precipitate by repeating step (f),
(h) regenerating (−)-1-benzyl-1,2,3,4-tetrahydroisoquinoline.

10. The process of claim 9 wherein all recrystallization are repeated twice.

* * * * *